United States Patent [19]

Takayama

[11] Patent Number: 4,559,928
[45] Date of Patent: Dec. 24, 1985

[54] ENDOSCOPE APPARATUS WITH MOTOR-DRIVEN BENDING MECHANISM

[75] Inventor: Syuichi Takayama, Tokyo, Japan

[73] Assignee: Olympus Optical Co., Ltd., Tokyo, Japan

[21] Appl. No.: 701,657

[22] Filed: Feb. 15, 1985

Related U.S. Application Data

[63] Continuation of Ser. No. 435,707, Oct. 21, 1982, abandoned.

[30] Foreign Application Priority Data

Oct. 22, 1981 [JP] Japan .............................. 56-168949
Oct. 22, 1981 [JP] Japan .............................. 56-168950

[51] Int. Cl.⁴ .............................................. A61B 1/06
[52] U.S. Cl. ...................................... 128/6; 318/305
[58] Field of Search ................................ 128/4–8; 318/293, 305, 490

[56] References Cited

U.S. PATENT DOCUMENTS

| | | | |
|---|---|---|---|
| 1,121,786 | 12/1914 | Barnum | 318/305 |
| 2,676,292 | 4/1954 | Spencer | 318/305 |
| 2,680,818 | 6/1954 | Ringwald | 318/490 |
| 3,641,410 | 2/1972 | Vogelsberg | 318/305 |
| 3,730,632 | 5/1973 | Chikama | 128/6 |

FOREIGN PATENT DOCUMENTS

| | | | |
|---|---|---|---|
| 2504663 | 8/1976 | Fed. Rep. of Germany | 128/4 |
| 2713749 | 10/1977 | Fed. Rep. of Germany | 128/4 |
| 1442487 | 7/1976 | United Kingdom | 318/305 |

Primary Examiner—Edward M. Coven
Assistant Examiner—Max F. Hindenburg

[57] ABSTRACT

An endoscope is disclosed which comprises: an insertion section having a flexible tube which is inserted into a body cavity and deflected or bent in the desired direction and a distal end portion coupled to the flexible tube; and a control section which is controlled by the operator such as a doctor. In the control section are disposed a motor which is reversible in response to switching operation of switches manually pressed by the operator and a motor-driven bending mechanism including a drum and an angulation wire to angulate or deflect the flexible tube. The angulation wire extends within the insertion section such that the distal end of the angulation wire is secured to a portion near the distal end portion of the flexible tube. Since the motor changes a rotational torque in accordance with the switching operation of the switch, the deflection speed of the flexible tube is changed.

7 Claims, 18 Drawing Figures

ENDOSCOPE APPARATUS WITH MOTOR-DRIVEN BENDING MECHANISM

This application is a continuation, of application Ser. No. 435,707, filed Oct. 21, 1982, now abandoned.

BACKGROUND OF THE INVENTION

The present invention relates to an endoscope apparatus and, more particularly, to an endoscope apparatus having a bending mechanism driven by a motor to bend an insertion section of the endoscope apparatus.

In a conventional endoscope apparatus, an insertion section is manually deflected or bent when the operator controls an angle-knob at a main body (control section) of the endoscope. An endoscope apparatus has been recently developed in which a bending mechanism is driven by a motor. According to conventional endoscope apparatuses having motor-driven bending mechanisms and respectively disclosed in Japanese Utility Model Disclosure Nos. 51-45790 and 51-91989 or Japanese Patent Disclosure No. 56-13455, a flexible tube of the insertion section can be controlled by the ON/OFF state of the motor operated by the operator. Therefore, the flexible tube is bent in accordance with a given torque obtained by the motor which is driven at a given speed. In other words, the flexible tube is bent at a given speed. When the bending speed of a flexible tube inserted into a body cavity is increased, the flexible tube overruns against the will of the operator. The flexible tube may abut against the wall of the body cavity and cause damage to the wall. The bending operation is difficult to perform properly when the bending speed of the flexible tube is high. The operator cannot control the flexible tube under his/her operation. If the bending speed of the flexible tube is decreased, the above problem can be solved, however, the examination becomes time-consuming and inefficient. In the conventional motor-driven endoscope apparatus having an insertion section which is bent at a given speed, an effective and safe endoscopic examination is difficult to perform.

The conventional endoscope apparatus of the type described above has another drawback. It is hard to perform an insertion section-bending operation in a desired manner. The distal end of the insertion section which is inserted in the body cavity undesirably abuts against the wall of the body cavity and continues to be deflected against the wall of the body cavity, so that the surface tissue of the body cavity may be hurt or cut, thus endangering the patient.

In order to solve the above problem, an endoscope apparatus is disclosed in Japanese Utility Model Disclosure No. 51-91990. According to this endoscope apparatus, a friction clutch is disposed between a bending mechanism and a motor. When the distal end of the insertion section contacts the wall of the body cavity of a patient and when a predetermined load is applied to the bending mechanism, the friction clutch slips to prevent an overload from being applied to the wall of the body cavity. However, in the conventional endoscope apparatus of the type described above, if the distal end of the insertion section contacts the inner wall of the body cavity, even when the friction clutch slips to decrease the transmission ratio of the driving force of the motor, a given driving force is still continuously applied to the bending mechanism. As a result, the distal portion of the insertion section continues to be urged against the inner wall of the body cavity, and the patient may feel pain or be hurt. Furthermore, since there is no means for positively signalling the above condition to the operator, the operator may not immediately know of the above condition. The distal end of the insertion section may continue to hurt or cut the inner wall of the body cavity of the patient. Thus, even in the endoscope apparatus of the type described above, a sufficiently effective and safe endoscopic examination cannot be performed.

SUMMARY OF THE INVENTION

It is, therefore, an object of the present invention to provide a new and improved endoscope apparatus wherein a driving force generated by a motor to bend an insertion section which is inserted into a body cavity is properly changed to effectively adjust the bending operation of the insertion section.

An endoscope apparatus in accordance with the present invention comprises an elongated insertion section to be inserted into a body cavity and freely deflected or bent in a desired direction, and an endoscope main body coupled to the insertion section and having various control switches to be operated by an operator. A motor device is arranged in the endoscope main body to receive electric power and generate a torque to bend the insertion section. A bending mechanism is mechanically coupled between the motor device and the insertion section for bending the insertion section in the desired direction in accordance with the torque from the motor device. Electrically connected to the motor device is a motor control device which adequately changes the electric power supplied to the motor device at a suitable time, thereby controlling the motor device in accordance with the amount of torque from the motor device. The deflection speed and deflection force of the insertion section of the endoscope apparatus can vary as needed in accordance with various situations.

BRIEF DESCRIPTION OF THE DRAWINGS

The present invention is best understood by reference to the accompanying drawings, in which.

DETAILED DESCRIPTION OF THE PREFERRED EMBODIMENTS

Figure 1:
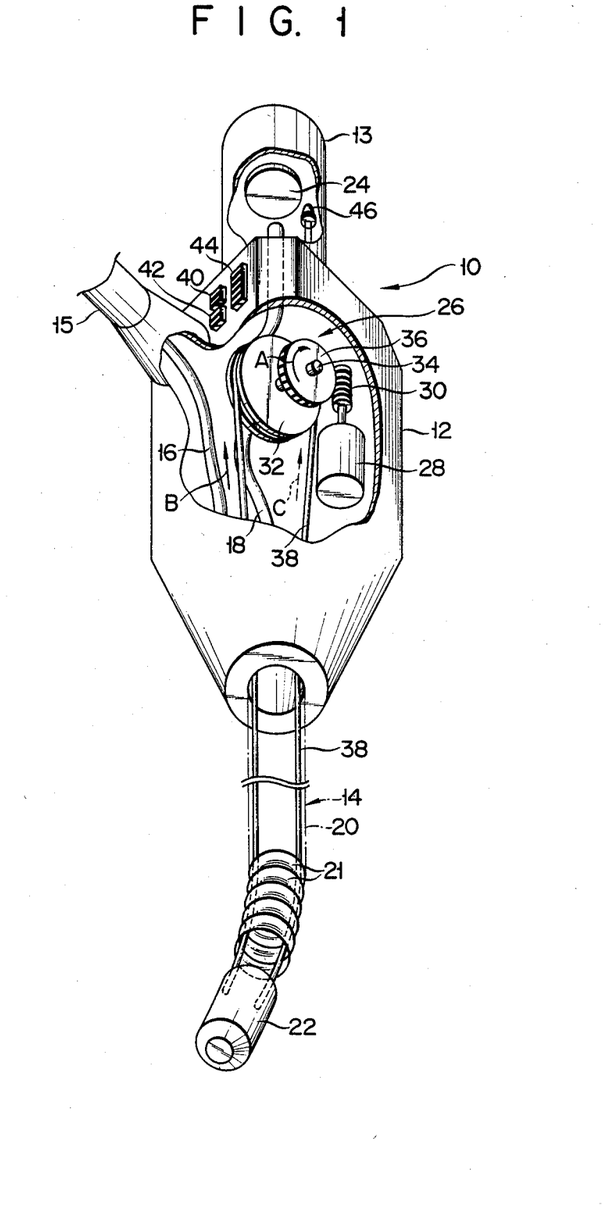
FIG. 1 is a partially cutaway perspective view showing the internal construction of the main part of an endoscope apparatus according to a first embodiment of the present invention.

Referring now to FIG. 1, an endoscope 10 comprises an endoscope main body (control section) 12, an eyepiece section 13 disposed on the control section 12, an elongated insertion section 14 connected to the lower end of the control section 12, and a light guide cord or universal cord 15 extending from the side portion of the control section 12. The universal cord 15 is detachably connected to a light source (not shown) by a known means. A light guide 16 extends through the universal cord 15, the control section 12 and the insertion section 14 in a known manner. An image guide 18 is provided extending through the insertion section 14, the control section 12 and the eyepiece section 13 in a known manner.

The insertion section 14 includes a flexible tube 20 comprising helical metal strips 21, and a known endoscope distal end portion 22 mounted at the free end of the flexible tube 20. The image guide 18 which comprises a bundle of flexible optical fibers receives an optical image at its incident end located inside the distal end portion 22 and transmits it to the eyepiece section 13. The light transmitting end of the image guide 18 which is located in the eyepiece section 13 opposes an ocular lens 24 disposed in the eyepiece section 13.

A motor-driven bending mechanism 26 is disposed in the control section 12. The motorized deflection mechanism 26 includes a reversible electric motor 28. A worm gear 30 is secured to the rotating shaft of a motor 28. A wire drum 32 which has a groove along its outer circumferential surface has a rotating shaft 34 and is coaxial with a spur gear 36 which meshes with the worm gear 30. An angulation wire 38 is looped in the groove of the wire drum 32 and extends through the control section 12 and the flexible tube 20 of the insertion section 14. The two ends of the angulation wire 38 are respectively connected to predetermined positions of the flexible tube 20 which are adjacent to the distal end portion 22 of the insertion section 14. Control switches 40, 42 and 44 are arranged on the outer surface of the control section 12, so that the operator such as a doctor can manually perform the deflection operation with them. In FIG. 1, reference numeral 46 denotes a light-emitting diode (LED) which is arranged adjacent to the ocular lens 24 of the eyepiece section 13 so as to signal to the operator who observes a body cavity through the eyepiece section 13.

Figure 2:
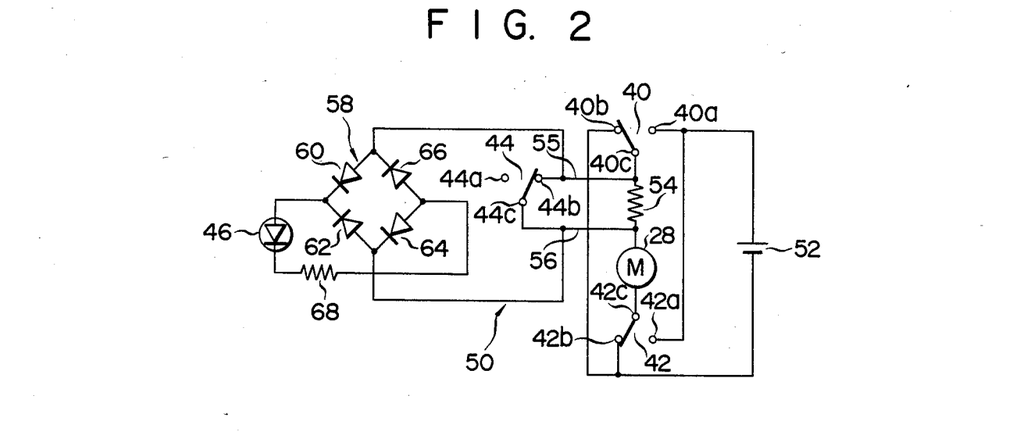
FIG. 2 is a circuit diagram showing the arrangement of a bending control circuit of the endoscope apparatus shown in FIG. 1.

FIG. 2 shows a circuit diagram of a control circuit 50 of the motor-driven bending mechanism shown in FIG. 1. The positive terminal of a DC power source 52 is connected to normally open contacts 40a and 42a of the control switches 40 and 42, respectively. The negative terminal of the DC power source 52 is connected to normally closed contacts 40b and 42b of the control switches 40 and 42, respectively. The motor 28 is connected between common contacts 40c and 42c of the control switches 40 and 42, respectively. A resistor 54 having a predetermined resistance is connected between the motor 28 and the common contact 40c of the control switch 40. Lines 55 and 56 connected to the two ends of the resistor 54 are respectively connected to a normally closed contact 44b and to a common contact 44c of the control switch 44.

The lines 55 and 56 are respectively connected to the input terminals of a bridge circuit 58 constituted by diodes 60, 62, 64 and 66 in a known manner. The LED 46 is connected between the output terminals of the bridge circuit 58 through a resistor 68.

The mode of operation of the endoscope apparatus having such motor-driven bending mechanism according to the first embodiment of the present invention will be described in detail. When the operator presses the control switch 40, the common contact 40c is connected to the normally open contact 40a. A current flows through the motor 28 through the normally open contact 40a of the switch 40 and the normally closed contact 44b of the switch 44. Thus, the motor 28 is rotated in the forward direction. Upon forward rotation of the motor 28, the spur gear 36 is rotated via the worm gear 30 in the direction indicated by arrow A. The wire drum 32 is then also rotated in the same direction. Upon rotation of the wire drum 32, the angulation wire 38 is pulled in the direction indicated by solid arrow B, and the flexible tube 20 of the insertion section 14 is bent upward. When the distal end portion 22 reaches a desired position, the operator releases the control switch 40, so that the common contact 40c is connected to the normally closed contact 40b. Thus, the distal end portion 22 is fixed in the desired position. When the operator wishes to deflect or bend the distal end portion 22 in the opposite direction, he presses the control switch 42 to connect the common contact 42c to the normally open contact 42a. A current flows through the normally open contact 42a of the control switch 42, the motor 28, the normally closed contact 44b of the control switch 44, and the normally closed contact 40b of the control switch 40 in the above order. Thus, the motor 28 is rotated in the reverse direction. Upon reverse rotation of the motor 28, the spur gear 36 is rotated via the worm gear 30 in the direction opposite to the direction indicated by arrow A. The angulation wire 38 is then pulled in the direction indicated by arrow C, and the flexible tube 20 of the insertion section 14 is bent downward. In this manner, when the operator presses the control switch 40 or 42, the motor is rotated in the forward or reverse direction, and hence the flexible tube 20 of the insertion section 14 is deflected upward or downward.

A case will be described in which the flexible tube 20 of the insertion section 14 must be bent to a small degree. In this case, the operator uses the control switch 44 and one of the control switches 42 and 44. For example, when the operator presses the control switches 40 and 44, the control switch 40 is switched to the normally open contact 40a and the control switch 44 is disconnected. A current flows through the motor 28 via the normally open contact 40a of the control switch 40 and the resistor 54. The current flowing in the motor 28 is thus attenuated by the resistor 54, so that the motor 28 is rotated at a low speed and the angulation wire 38 is gradually pulled via the worm gear 30, the spur gear 36 and the wire drum 32 in the direction indicated by solid arrow B. Thus, the flexible tube 20 of the insertion section 14 is gradually bent so as to slightly change the position of the distal end portion 22 thereof. At this time, since the voltage across the resistor 54 is applied across the input terminals of the bridge circuit 58, the LED 46 goes on to indicate the low-speed deflecting operation. In this manner, when the operator presses the control switch 44, the flexible tube 20 of the insertion section 14 is gradually bent so as to slightly change the position of the distal end portion 22 thereof, thus providing excellent operability for the endoscopic examination. In other words, the torque generated by the motor 28 to deflect the insertion section 14 inserted in the body cavity is properly changed in accordance with the switching operation by the operator. Thus, the bending speed of the flexible tube 20 of the insertion section 14 can be minutely adjusted in a desired manner. Therefore, the insertion section 14 will not overrun against the will of the operator, thereby greatly decreasing the danger of the distal end portion 22 damaging the tissue of the wall of the body cavity, and providing safe endoscopic examination and therapy.

Figure 3:
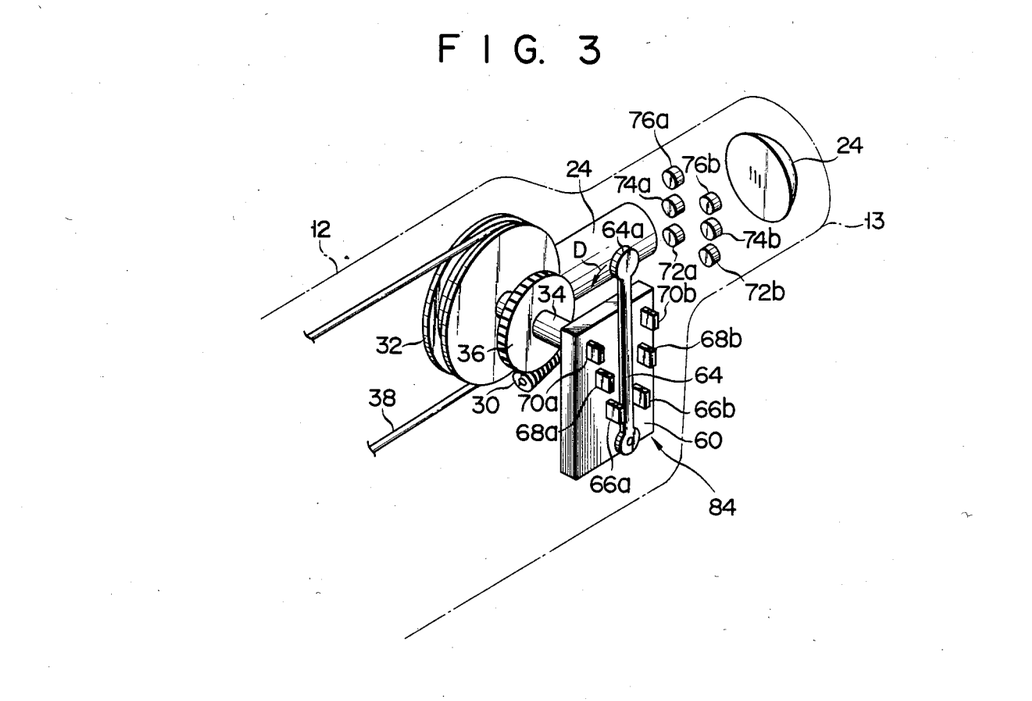
FIG. 3 is a partial perspective view schematically showing the main part of an endoscope apparatus according to a second embodiment of the present invention.
Figure 4:
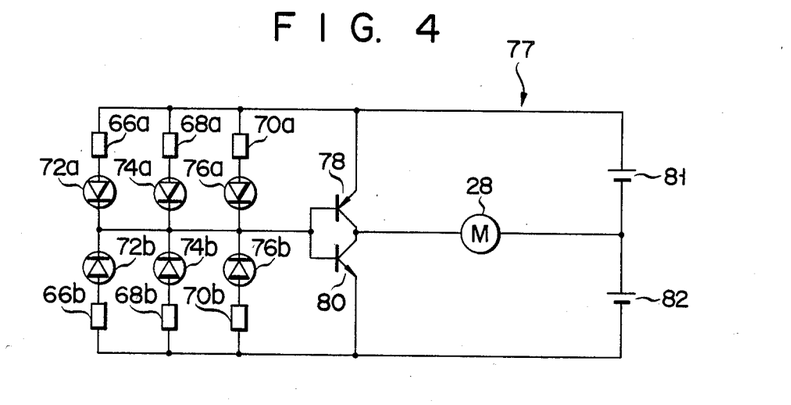
FIG. 4 is a circuit diagram showing the arrangement of a bending control circuit of the endoscope apparatus shown in FIG. 3.

FIGS. 3 and 4 respectively illustrate the main part of an endoscope apparatus according to a second embodiment of the present invention, and its circuit diagram. The same reference numerals used in FIGS. 1 and 2 denote the same or similar parts in FIGS. 3 and 4, and a detailed description thereof will be omitted. Referring to FIG. 3, a spur gear 36 which meshes with a worm gear 30 is mounted on a rotating shaft 34 of a wire drum 32. A lever support plate 60 is mounted on the rotating shaft 34 of the wire drum 32. A deflection control lever 64 is disposed on the lever support plate 60 to be pivotal about the proximal end portion of the lever support plate 60. A control knob 64a of the deflection control lever 64 extends from the interior of an endoscope control section 12 to the outside, and can be manually controlled by the operator. Three pairs of piezoelectric rubber portions 66a and 66b, 68a and 68b, and 70a and 70b are disposed to sandwich the pivotable deflection control lever 64. The three pairs of piezoelectric rubber portions 66a and 66b, 68a and 68b, and 70a and 70b are respectively symmetrical about the deflection control lever 64 when it is held in the neutral position shown in FIG. 3. The resistances of the piezoelectric rubber portions are respectively changed in accordance with an external force applied thereto. The distances between the piezoelectric rubber portions which constitute the three pairs are gradually increased in the direction toward the control knob 64a of the deflection control lever 64. When the operator moves the deflection control lever 64 in the direction indicated by arrow D, a portion of the lever 64 first contacts the lowest piezoelectric rubber portion 66a. When the operator further moves the lever 64 in the direction indicated by arrow D, the lever 64 sequentially contacts the intermediate piezoelectric rubber portion 68a and the highest piezoelectric rubber portion 70a.

LEDs 72a and 72b, 74a and 74b, and 76a and 76b are arranged in an eyepiece section 13 and respectively correspond to the piezoelectric rubber portions 66a and 66b, 68a and 68b, and 70a and 70b. In a circuit 77 of FIG. 4, the LEDs 72a and 72b, 74a and 74b, and 76a and 76b are respectively connected to the piezoelectric rubber portions 66a and 66b, 74a and 74b, and 76a and 76b, as shown in FIG. 4. The piezoelectric rubber portions 66a, 68a and 70a are commonly connected to the bases of a PNP transistor 78 and an NPN transistor 80 through the LEDs 72a, 74a and 76a, respectively. Similarly, the piezoelectric rubber portions 66b, 68b and 70b are commonly connected to the bases of the PNP transistor 78 and the NPN transistor 80 through the LEDs 72b, 74b and 76b, respectively. The emitter of the PNP transistor 78 is connected to one end of each of the piezoelectric rubber portions 66a, 68a and 70a, and also to the positive terminal of a DC power source 81. Similarly, the emitter of the NPN transistor 80 is connected to one end of each of the piezoelectric rubber portions 66b, 68b and 70b, and also to the negative terminal of a DC power source 82. The collectors of the transistors 78 and 80 are commonly connected to one end of a motor 28. A common node between the DC power sources 81 and 82 is connected to the other end of the motor 28.

In the second embodiment shown in FIGS. 3 and 4, when the deflection control lever 64 is brought into tight contact with the piezoelectric rubber portions 66a, 68a and 70a, or 66b, 68b and 70b, the rotational direction and rotational speed of the motor 28 are controlled. For example, when the operator moves the lever 64 in the direction indicated by arrow D, so that the lever 64 urges against the piezoelectric rubber portion 66a, the resistance of the piezoelectric rubber portion 66a is decreased. A base current then flows through the NPN transistor 80 via the piezoelectric rubber portion 66a and the LED 72a. A collector current which is an $h_{fe}$ (small-signal short-circuit forward current transfer ratio) multiple of the base current flows through the NPN transistor 80. The motor 28 is driven in the forward direction at a speed corresponding to the collector current of the NPN transistor 80. Upon rotation of the motor 28, the spur gear 36 and the wire drum 32 are rotated, so that the flexible tube 20 of the bending section 14 is deflected. At this time, upon rotation of the wire drum 32, a lever support plate 60 of a control unit 84 is pivoted. Thus, the operator knows the bending angle by the position of the deflection control lever 64. When the operator presses the lever 64 hard in the direction indicated by arrow D, it is brought into tight contact with the piezoelectric rubber portions 66a and 68a; or 66a, 68a and 70a. The piezoelectric rubber portions 66a and 68a; or 66a, 68a and 70a are rendered conductive, so that a base current flowing through the NPN transistor 80 is increased. A current flowing through the motor 28 is then increased to increase the rotational speed of the motor 28. Therefore, the bending speed of the flexible tube 20 of the insertion section 14 is increased. In this manner, the bending speed or deflection speed can be changed in accordance with the degree of a force applied to the deflection control lever 64. When the operator presses the deflection control lever 64 in the direction opposite to the direction indicated by arrow D, the motor 28 is rotated in the opposite direction at a speed corresponding to the number of piezoelectric rubber portions pressed by the force applied to the deflection control lever 64. Thus, the insertion section 14 is deflected in the opposite direction. The deflection speed of the flexible tube 20 of the insertion section 14 is indicated by the number of LEDs which go on. The greater the number of LEDs which go on, the faster the insertion section 14 is being driven.

Piezoelectric rubber portions are used in the control unit 84. However, microswitches 86, 88, and so on may be used in place of the piezolectric rubber portions (FIG. 5).

Figures 5, 6:
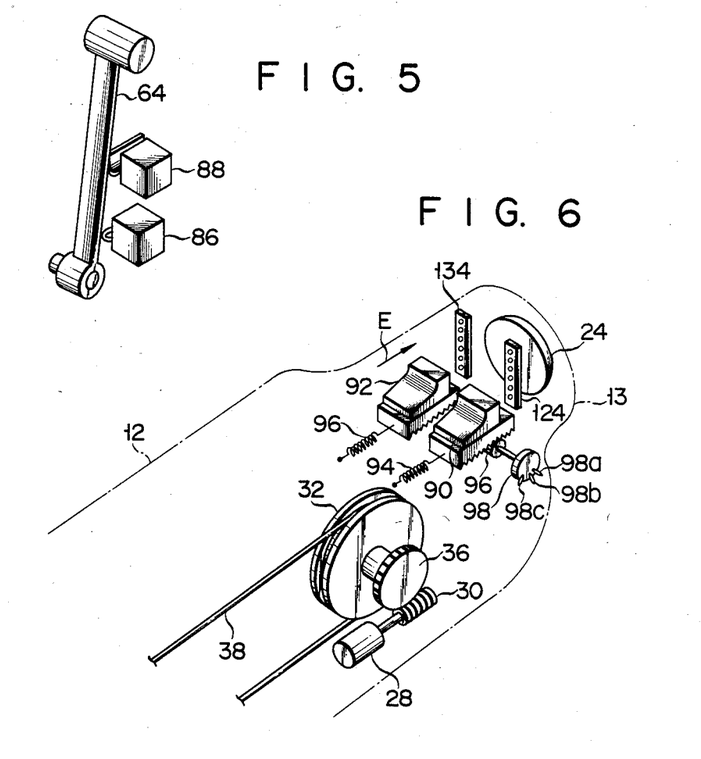
FIG. 5 is a partial perspective view showing a modification of a bending control lever using a microswitch in place of a piezoelectric rubber used in the endoscope apparatus shown in FIG. 3.
FIG. 6 is a partial perspective view schematically showing the main part of an endoscope apparatus according to a third embodiment of the present invention.
Figure 7:
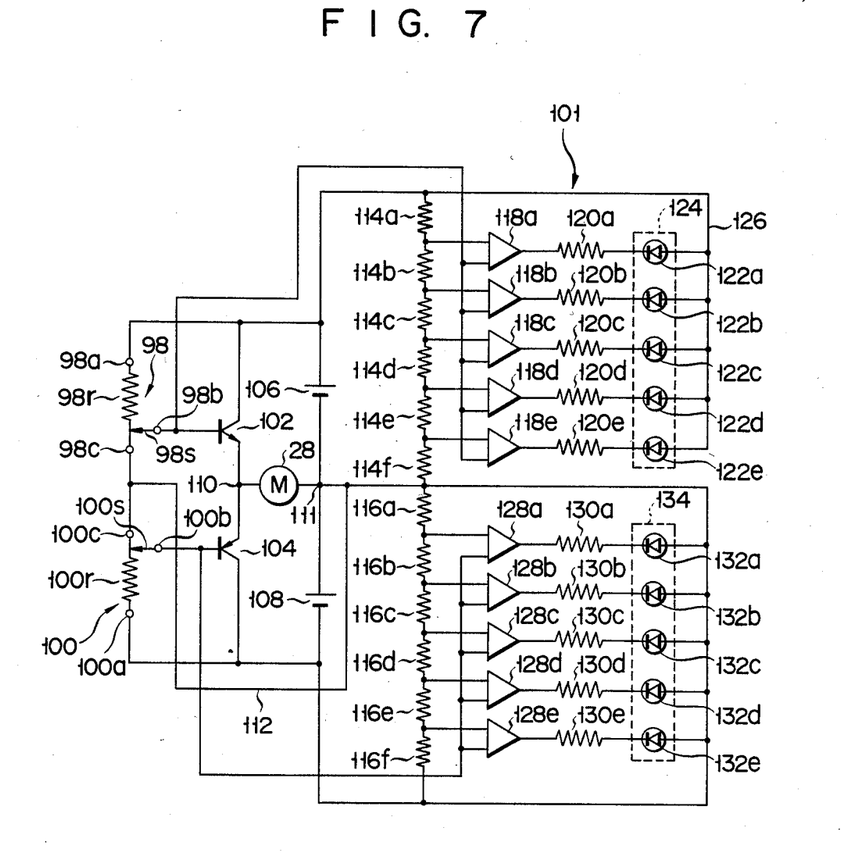
FIG. 7 is a circuit diagram of a bending control circuit of the endoscope apparatus shown in FIG. 6.

FIGS. 6 and 7 respectively show an endoscope apparatus according to a third embodiment of the present invention, and a circuit diagram of a control circuit thereof. Referring to FIG. 6, slide buttons 90 and 92 are arranged in an endoscope control section 12 so as to be linearly slidable along the longitudinal direction of the control section 12. Elastic members such as coil springs 94 and 96 are respectively mounted to the slide buttons 90 and 92 in the control section 12. The operator slides the slide button 90 or 92 against the urging force of the spring 94 or 96 in the direction indicated by arrow E. When the external force is withdrawn from the slide button 90 or 92, the slide button 90 or 92 is returned to the normal position (the position indicated in FIG. 6) by the urging force of the spring 94 or 96.

Gear teeth are formed on the rear surface of the slide buttons 90 and 92 which then serve as rack gears, respectively. The slide buttons 90 and 92 as the rack gears mesh with pinion gears 96, respectively. Sliders 98s and 100s (FIG. 7) of potentiometers 98 and 100 are secured to the pinion gears 96, respectively (the potentiometer 100 is not illustrated in FIG. 6 but only in the circuit diagram in FIG. 7). Referring to FIG. 7, when the operator does not slide the slide buttons 90 and 92, the slide buttons 90 and 92 are held in the normal positions shown in FIG. 6. The sliders 98s and 100s of the potentiometers 98 and 100 are located at the nearest positions to resistors 98r and 100r in the potentiometers 98 and 100. At this time, the resistors 98r and 100r have the maximum resistances. In the normal position, a resistance between a first terminal 98a and a common slider terminal 98b of the potentiometer 98 is maximum. Similarly, a resistance between a first terminal 100a and a common slider terminal 100b is maximum. The slide buttons 90 and 92 are arranged in a known manner such that they may not be simultaneously slid in the same direction.

In the deflection control circuit 101 shown in FIG. 7, the potentiometers 98 and 100 respectively mounted on the pinion gears 96 are connected in series with each other. The common slider terminals 98b and 100b of the potentiometers 98 and 100 are connected to the base of an NPN transistor 102 and the base of a PNP transistor 104, respectively. The emitter of the NPN transistor 102 is connected to the emitter of a PNP transistor 104. The NPN transistor 102 has its collector connected to the first terminal 98a of the potentiometer 98 and to the positive terminal of a DC power source 106. The PNP transistor 104 has its collector connected to the first terminal 100a of the potentiometer 100 and to the negative terminal of a DC power source 108. The negative terminal of the DC power source 106 is connected to the positive terminal of the DC power source 108. The motor 28 is connected between a common node 110 of the transistors 102 and 104 and a common node 111 of the DC power sources 106 and 108. The common node 111 of the DC power sources 106 and 108 is commonly connected to second terminals 98c and 100c of the potentiometers 98 and 100, respectively, through a line 112.

A series circuit comprising a plurality of voltage-dividing resistors 114 (six resistors 114a to 114f in this embodiment) is connected in parallel with the DC power source 106. Similarly, a series circuit comprising a plurality of voltage-dividing resistors 116 (six resistors 116a to 116f in this embodiment) is connected in parallel with the DC power source 108. Each one of common nodes of pairs of adjacent resistors (e.g., common nodes between the resistors 114a and 114b, between the resistors 114b and 114c, and so on) among the plurality of voltage-dividing resistors 114 is connected to one input terminal of each of five comparators 118. The other input terminal of each of the comparators 118 is connected to the base of the NPN transistor 102. The output terminals of the comparators 118a, 118b, 118c, 118d and 118e are respectively connected to cathodes of LEDs 122 (five LEDs 122a to 122e in this embodiment) which constitute a display array 124 through resistors 120, respectively, (five resistors 120a to 120e in this embodiment). The anodes of the LEDs 122 are commonly connected to a line 126 which is, in turn, connected to the positive terminal of the DC power source 106. Similarly, one input terminal of each of comparators 128 (five comparators 128a to 128e in this embodiment) is connected to the common nodes of pairs of adjacent resistors 116. Each one of the comparators 128 has its other input terminal connected to the base of the PNP transistor 104. The output terminals of the comparators 128 are commonly connected to the common node 111 of the DC power sources 106 and 108 through resistors 130, respectively, (five resistors 130a to 130e in this embodiment) and to LEDs 132 (five LEDs 132a to 132e in the embodiment) of which the latter constitute a display array 134, and to the negative terminal of the DC power source 108.

In the above embodiment shown in FIGS. 6 and 7, the bending speed of the insertion section 14 can be changed in accordance with the degree of the force applied to the slide button 90 or 92. For example, when the operator slides the slide button 90, the slider 98s of the potentiometer 98 is moved in accordance with displacement of the slide button 90, and a current flowing through the base of the NPN transistor 102 is changed. A current which is an $h_{fe}$ multiple of the base current flows in the motor 28 through the collector of the NPN transistor 102. The insertion section 14 is then deflected in accordance with a rotational speed of the motor 28. At this time, a voltage appearing at the common slider terminal 98b is supplied to the comparators 118a to 118e and is compared thereby with divided voltages from the resistors 114a and 114f. Outputs from the comparators 118a to 118e are supplied to turn on the LEDs of the display array 124 in accordance with a voltage at the common slider terminal 98b. The operator can confirm the deflection speed of the insertion section 14 in accordance with the number of LEDs which go on. In this embodiment, since the potentiometers 98 and 100 are used to continuously change the deflection speed of the insertion section 14, the operability of the endoscope apparatus is greatly improved and fine adjustment can be performed.

Figure 8:
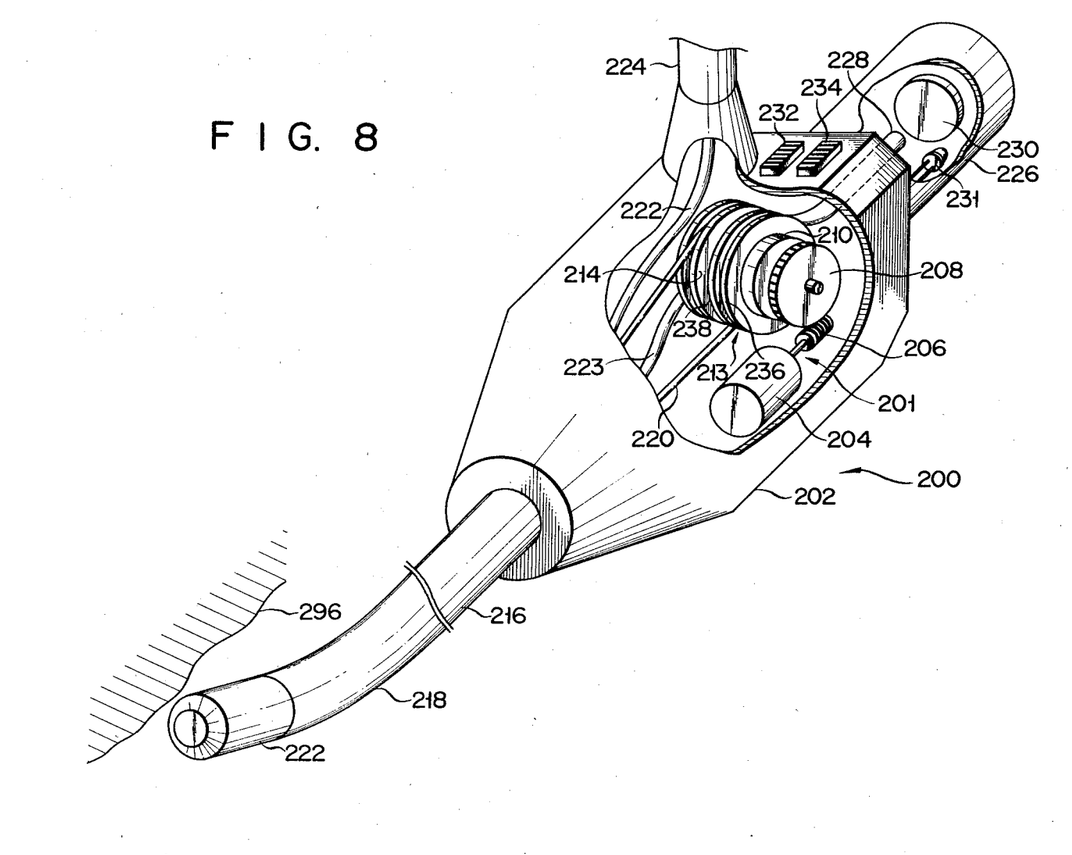
FIG. 8 is a partially cutaway perspective view showing the internal construction of the main part of an endoscope apparatus according to a fourth embodiment of the present invention.

Referring now to FIG. 8, there is illustrated an endoscope 200 having a motor-driven bending mechanism 201 according to a fourth embodiment of the present invention. A reversible motor 204 is arranged in an endoscope control section 202. A worm gear 206 is mounted on the rotating shaft of the motor 204 and meshes with a worm wheel 208. A first friction plate 210 which gangs with the worm wheel 208 is secured to the worm wheel shaft. A second friction plate 212 (FIG. 9) opposes the first friction plate 210. The first and second friction plates 210 and 212 constitute a friction clutch 213 and are brought into tight contact with each other by a pressure means (not shown). A wire drum 214 is coaxial with the second friction plate 212. An angulation wire 220 is looped in a groove formed in the outer circumferential surface of the wire drum 214 and is pulled to deflect a flexible tube 218 of an insertion section 216 coupled to the endoscope control section 202. The flexible tube 218 is bent when the angulation wire 220 is pulled upon rotation of the reversible motor 204. A distal end portion 222 of the flexible tube 218 can be deflected in any disired direction.

A light guide 222 and an image guide 223 are disposed within the control section 202 and the insertion section 216. The light guide 222 further extends through a universal cord 224 connected to the side portion of the control section 202 and is connected to a light source (not shown). The image guide 223 extends through any eyepiece section 226, and its light transmitting end 228 opposes an ocular lens 230 in the eyepiece section 226. An LED 231 is arranged in the control section 202 to be adjacent to the ocular lens. First and second switches 232 and 234 are arranged in the control section 202 to determine the rotational direction of the motor 204.

Figures 9, 10, 11:
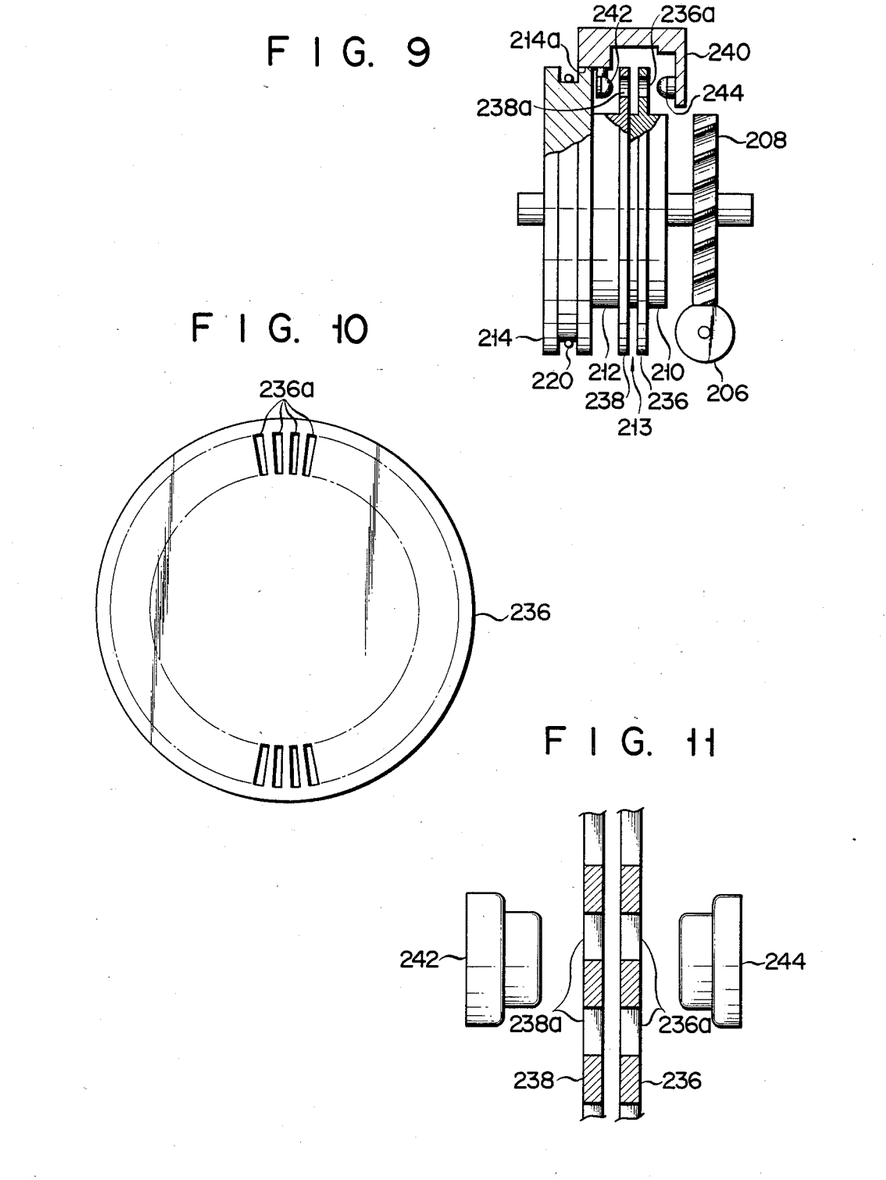
FIG. 9 is a partially cutaway side view of the main part of the bending mechanism of the endoscope apparatus shown in FIG. 8, including a wire drum, a friction clutch and a clutch slippage detector device.
FIG. 10 is a plan view of one of the friction plates included in the friction clutch shown in FIG. 9.
FIG. 11 is a view showing a model for explaining the positional relationship between a plurality of slits formed in each of the friction plates and light-receiving and light-emitting elements constituting the clutch slippage detector device shown in FIG. 9.

FIG. 9 shows the friction clutch 213 and its related mechanism in detail. A flange 236 is formed on the periphery of the first friction plate 210 coaxial with the worm wheel 208. As shown in FIG. 10, a plurality of elongated slits 236a are radially formed near the peripheral portion of the flange 236. Similarly, as shown in FIG. 9, a flange 238 opposing the flange 236 is formed on the periphery of the second friction plate 212 connected to the wire drum 214. A plurality of slits 238a having the same size and shape as the slits 236a are radially formed near the peripheral portion of the flange 238.

Figure 12:
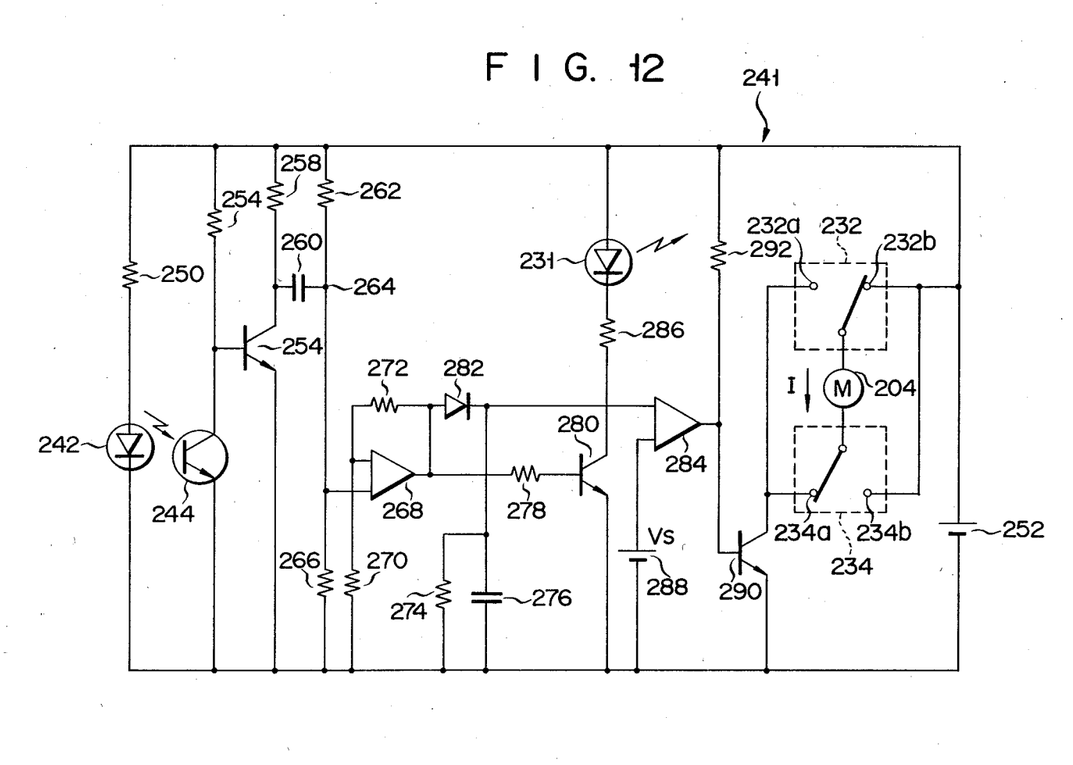
FIG. 12 is a circuit diagram of a bending control circuit of the endoscope device shown in FIG. 8.

Referring to FIG. 9, a support table 240 rotatable together with the wire drum 214 is secured at a portion 214a of the periphery of the wire drum 214. The support table 240 has a recess so as to house the periphery of the flanges 236 and 238 therein. Spaces are respectively formed between the support table 240 and the flange 236 and between the support table 240 and the flange 238 so that they will not contact each other when the friction plates 210 and 212 are rotated. A light-emitting diode (LED) 242 and a phototransistor 244 are arranged inside the support table 240. The LED 242 and the phototransistor 244 oppose each other through the slits 236a of the flange 236 of the first friction plate 210 and through the slits 238a of the flange 238 of the second friction plate 212. FIG. 11 is a plan view showing the positional relationship between the LED 242 and the flange 238 and between the phototransistor 244 and the flange 236. FIG. 12 shows a circuit diagram of a bending control circuit of the endoscope apparatus shown in FIG. 8.

In a motor control circuit 241 of FIG. 12, a series circuit of the LED 242 and a resistor 250 and a series circuit of the phototransistor 244 and a resistor 254 are commonly connected between the positive and negative terminals of a DC power source 252. The collector of the phototransistor 244 is connected to the base of an NPN transistor 256. The collector of the NPN transistor 256 is connected to the positive terminal of the DC power source 252 through a resistor 258 and is further connected to the positive terminal of the DC power source 252 through a capacitor 260 and a resistor 262. A common node 264 between the capacitor 260 and the resistor 262 is connected to the negative terminal of the DC power source 252 through a resistor 266 and to the first input terminal of an operational amplifier 268. The second input terminal of the operational amplifier 268 is connected to the negative terminal of the DC power source 252 through a resistor 270 and to the output terminal thereof through a resistor 272. The output terminal of the operational amplifier 268 is also connected to the negative terminal of the DC power source 252 through a parallel circuit of a resistor 274 and a capacitor 276. The output terminal of the operational amplifier 268 is further connected to an NPN transistor 280 through a resistor 278 and to the first input terminal of a comparator 284 through a diode 282. The collector of the NPN transistor 280 is connected to the positive terminal of the DC power source 252 through a resistor 286 and a display LED 231 shown in FIG. 8.

A reference voltage source 288 for generating a reference voltage Vs is connected to the second input terminal of the comparator 284 in a manner as shown in FIG. 12. The output terminal of the comparator 284 is connected to the base of an NPN transistor 290 and to the positive terminal of the DC power source 252 through a resistor 292. The collector of the NPN transistor 290 is connected to contacts 232a and 234a of first and second control switches 232 and 234, respectively. The first and second control switches 232 and 234 are connected to each other through the motor 204. Contacts 232b and 234b of the first and second control switches 232 and 234 respectively are commonly connected to the positive terminal of the DC power source 252. It is noted that the control switches 232 and 234 are respectively switched to the contacts 232a and 234a in normal condition.

The mode of operation of the above endoscope apparatus will be described below. When the operator inserts the insertion section 216 into a body cavity and presses the first control switch 232, the first control switch 232 is switched to the contact 232b. A current I flows in the direction indicated in FIG. 12, and the motor 204 is rotated in the forward direction. The driving force of the motor 204 is transmitted to the flexible tube 218 through the worm gear 206, the worm wheel 208, the first and second friction plates 210 and 212, the wire drum 214 and the angulation wire 220. Thus, the flexible tube 218 is deflected. The operator can observe a desired portion of the body cavity through the image guide 223 and the ocular lens 230 in the eyepiece section 226.

Figure 13A:
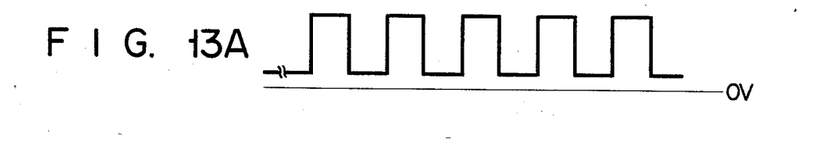
FIGS. 13A to 13F are timing charts showing the waveforms of the signals generated at the main part of the bending control circuit shown in FIG. 12.
Figure 13B:
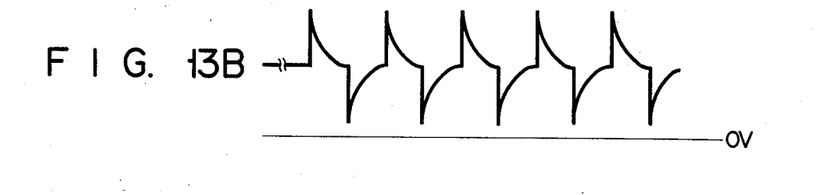

When the distal end portion 222 of the insertion section 216 contacts a wall 296 of the body cavity, a load applied to the angulation wire 220 for driving the bending mechanism is increased, so that slippage occurs between the first and second friction plates 210 and 212 Upon this slippage, the relative positions of the slits 236a and 238a of the flanges 236 and 238 are changed. Light rays which are emitted from the LED 242 and pass through the slits 236a and 238a are intermittentily interrupted and are incident on the phototransistor 244. The phototransistor 244 thus receives pulsed light rays to produce a pulse signal having a waveform shown in FIG. 13A. The pulse signal serves to turn ON/OFF the NPN transistor 256, so that a differentiation pulse signal having a spike waveform shown in FIG. 13B appears at the common node 264 between the capacitor 260 and the resistor 262. The differentiation pulse signal is amplified by the operational amplifier 268 which then produces a pulse signal having a waveform shown in FIG. 13C. The mesial magnitude of the differentiation pulse signal shown in FIG. 13B is predetermined by the voltage-dividing ratio of the resistor 262 to the resistor 266.

Figure 13C:
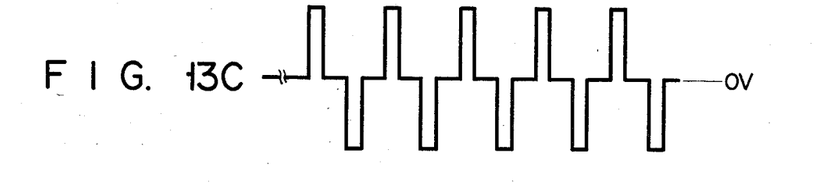
Figure 13D:
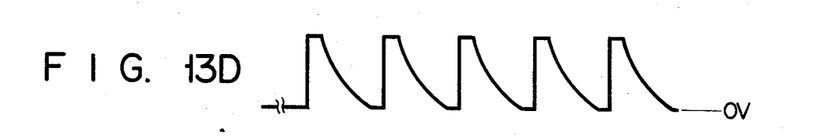
Figure 13E:
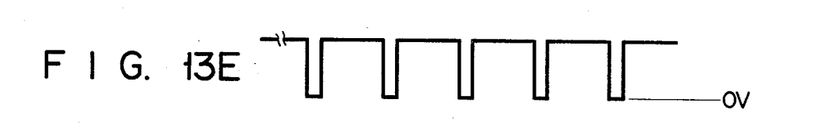
Figure 13F:
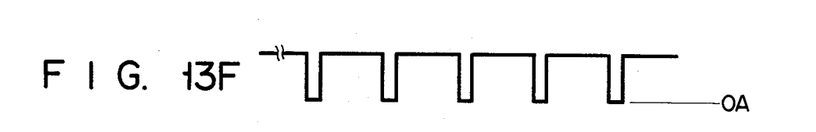

The signal shown in FIG. 13C is charged in the capacitor 276 through the diode 282, and a signal having a waveform shown in FIG. 13D is obtained. The signal shown in FIG. 13D is compared with the reference voltage Vs in the comparator 284, and the comparator 284 produces a signal having a waveform shown in FIG. 13E. When the signal shown in FIG. 13E is set to logic level "1", the NPN transistor 290 is ON. However, when the signal shown in FIG. 13E is set to logic level "0", the NPN transistor 290 is OFF. Upon the switching operation of the NPN transistor 290, the current flowing through the motor 204 is limited and has a waveform shown in FIG. 13F. Thus, the driving force of the motor 204 is attenuated. In other words, when the first and second friction plates 210 and 212 of the friction clutch 213 slip at a speed exceeding a predetermined speed, the current flowing through the motor 204 is decreased, thus decreasing the driving force thereof. A sufficient driving force is not transmitted to the angulation wire 220, so that the force applied by the distal end portion 222 urging against the wall 296 is decreased. Therefore, undesirable application of force to the wall 296 of the body cavity is properly prevented, thus assuring the safety of the body of the patient.

The signal appearing at the output terminal of the operational amplifier 268 is supplied to the NPN transistor 280 through a resistor 278. The NPN transistor 280 is ON/OFF in response to the signal shown in FIG. 13C. Upon ON/OFF operation of the NPN transistor 280, the display LED 231 arranged in the eyepiece section 226 flashes. Thus, the operator is made aware when the distal end portion 222 contacts the wall 296 of the body cavity, and the first and second friction plates 210 and 212 slip. While the operator can easily recognize flashing of the display LED 231, he can also observe the desired portion of the body cavity at the eyepiece section 226. At this time, when the operator presses the control switch 232 or 234 to withdraw power from the motor 204 or reverse the rotation of the motor 204, the distal end portion 222 is held at a position where it contacts the wall 296 of the body cavity, thus further assuring safety of the body of the patient.

In the endoscope apparatus according to the fourth embodiment of the present invention, when the distal end portion 222 of the insertion section 216 contacts the wall 296 of the body cavity, the torque of the motor 204 which is applied to the insertion section 216 is temporarily decreased or eliminated, so that the deflection of the insertion section 216 is effectively and properly adjusted.

Although the present invention has been shown and described with respect to the particular embodiments, nevertheless, various changes and modifications which are obvious to a person skilled in the art to which the invention pertains are deemed to lie within the spirit, scope and contemplation of the invention.

For example, in the embodiment shown in FIGS. 6 and 7, the two potentiometers 98 and 100 are respectively disposed independently on the two pinion gears 96. However, one potentiometer can be used for the two pinion gears 96.

In the above embodiment, the flexible tube of the insertion section is deflected vertically. However, in practice, the flexible tube may be deflected in four directions. The configuration of the endoscope apparatus having the flexible tube which is vertically deflected is substantially the same as that of the endoscope apparatus having the flexible tube which is deflected in four directions, except that a pair of additional angulation wires are horizontally disposed with respect to the vertically disposed pair of angulation wires so as to form equal angular intervals between the four angulation wires.

In the embodiment shown in FIGS. 8 to 13, when the first and second friction plates 210 and 212 slip, the current flowing through the motor 204 is limited to decrease the driving force of the motor. By adjusting the constant of the resistor 274 and the capacitor 276, the charge time of the capacitor may be increased to temporarily stop the motor 204 when slippage occurs. The deflection of the insertion section 216 can be temporarily stopped, and the external force applied by the distal end portion 222 to the wall 296 of the body cavity can be eliminated. Furthermore, when the reference voltage Vs applied to the comparator 284 is decreased, slight slippage of the first and second friction plate 210 and 212 can be detected, thus limiting the deflection at an early point in time. In the above embodiment, slippage of the first and second friction plates 210 and 212 is optically detected. However, such slippage may be detected electrically or magnetically.

What is claimed is:

1. an endoscope apparatus comprising:
   (a) an elongated insertion section adapted to be inserted into a body cavity and freely bendable therein in a desired direction;
   (b) a main body, and an eyepiece section, both coupled to said insertion section;
   (c) motor means in said main body for receiving electric power and for generating torque to bend said insertion section;
   (d) bending means mechanically connected to said motor means and said insertion section, for bending said insertion section in accordance with the torque generated by said motor means;
   (e) an operation member provided at said endoscope main body and including a lever member to be manually operated by an operator;
   (f) bending speed controller means connected to said motor means and to said lever member and including level displacement detecting means disposed near said lever member for electrically detecting displacement of said lever member, said lever displacement detecting means consisting of a material the conductivity of which increases with increased pressure, said lever displacement detecting means including a plurality of detecting portions pressed in an order corresponding to the displacement of said lever member, and transistor circuit means connected to said lever displacement detecting means and said motor means for continuously increasing the power supplied to said motor means, between a minimum and a maximum level, in accordance with the displacement of said lever member, and
   (g) bending speed indicator means arranged in said eyepiece section and electrically connected to said lever member and said lever displacement detecting means, said bending speed indicator means comprising a plurality of light-emitting devices provided in said eyepiece section and which increase the amount of light emitted thereby, substantially in proportion to the displacement of said lever member, for indicating to the operator the actual speed level of said insertion section while looking in the eyepiece section, based on the amount of electrical power supplied to said motor means.

2. An endoscope apparatus according to claim 1, wherein said motor means includes an electric motor selectively driven in forward and reverse directions in accordance with the current flowing therethrough.

3. An endoscope apparatus according to claim 2, wherein said lever member is constructed to lean in a first and a second direction, and said bending speed controller means rotates said electric motor in a forward or revrse direction in response to said lever member leaning in the first or second direction, to thereby control the bending of said insertion section so as to selectively bend in one of opposite directions.

4. An endoscope apparatus according to claim 1, wherein said material of said lever displacement detecting means is piezoelectric rubber.

5. An endoscope apparatus according to claim 1, wherein said plurality of detecting portions comprise pairs of detecting portions, the detecting portions of each pair being respectively place on opposite sides of said lever member, the distance between detecting portions of adjacent pairs varying from each other.

6. An endoscope apparatus according to claim 5, wherein said pairs become conductive sequentially with increasing inclination of said lever member from a neutral position.

7. An endoscope apparatus according to claim 5, wherein said pairs of detecting portions are connected in parallel to said transistor circuit means.

* * * * *